United States Patent [19]

Caron

[11] Patent Number: 6,005,118

[45] Date of Patent: Dec. 21, 1999

[54] METHODS OF PREPARING 4-CYANO-4 (SUBSTITUTED INDAZOLE) CYCLOHEXANE-CARBOXYLIC ACIDS USEFUL AS PDE4 INHIBITORS

[76] Inventor: Stéphane Caron, 600 Meridian St., Groton, Conn. 06340

[21] Appl. No.: 09/153,762

[22] Filed: Sep. 15, 1998

Related U.S. Application Data

[60] Provisional application No. 60/064,211, Nov. 4, 1997.

[51] Int. Cl.$^6$ ..................... C07D 231/56; A61K 31/415
[52] U.S. Cl. ........................................ 548/362.5; 514/403
[58] Field of Search .................. 548/362.5, 514

[56] References Cited

FOREIGN PATENT DOCUMENTS 97-42174  11/1997  WIPO .

*Primary Examiner*—Floyd D. Higel
*Attorney, Agent, or Firm*—Peter C. Richardson; Paul H. Ginsburg; Raymond M. Speer

[57] ABSTRACT

An improved process for preparing a compound of Formula (I):

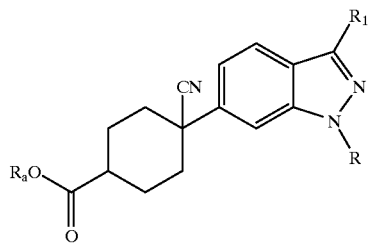

comprising:

(a) treating a compound of Formula (Ia):

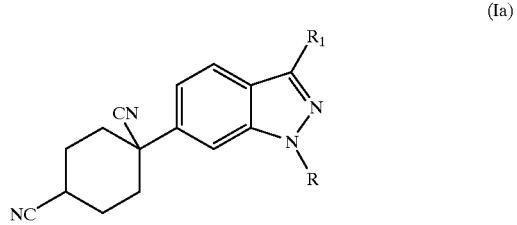

with an alcohol comprising a compound of Formula (Ib-A) and an acid comprising a compound of Formula (Ib-B):

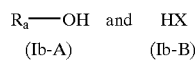

wherein
$R_a$ is selected from the group consisting essentially of hydrogen; $(C_1-C_6)$ alkyl; phenyl and $(C_1-C_3)$ alkyl-phenyl wherein said phenyl groups are optionally substituted by one or two substituents selected from the group consisting essentially of —$(C_1-C_4)$ alkyl; —$O(C_1-C_3)$ alkyl; Br; and Cl; and HX is an acid selected from the group consisting essentially of hydrobromic acid; hydrochloric acid; sulfuric acid; sulfonic acid; and aliphatic and aromatic sulfonic acids selected from the group consisting essentially of methanesulfonic acid, trifluoromethanesulfonic acid, benzenesulfonic acid, benzylsulfonic acid, p-toluene sulfonic acid, and camphorsulfonic acid, whereby HX provides the acidic conditions which result in formation of a salt of the corresponding imidate of Formula (Ic):

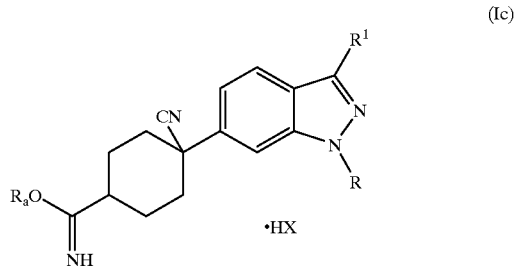

and
(b) hydrolyzing said compound of Formula (Ic) to provide said compound of Formula (I).

8 Claims, No Drawings

METHODS OF PREPARING 4-CYANO-4 (SUBSTITUTED INDAZOLE) CYCLOHEXANE-CARBOXYLIC ACIDS USEFUL AS PDE4 INHIBITORS

CROSS REFERENCE TO RELATED APPLICATIONS

This application is a continuation-in-part of provisional application Ser. No. 60/064,211, filed Nov. 4, 1997, priority of which is hereby claimed.

FIELD OF THE INVENTION

The present invention is in the field of methods for preparing complex heterocyle-containing organic compounds which have biological, and more especially, therapeutic activity. More particularly, the present invention is in the field of improved methods for preparing cyclohexanecarboxylic acids para-substituted by cyano and (substituted)indazole groups which posses advantages of manufacturing economy.

BACKGROUND OF THE INVENTION

The present invention relates to an improved method of preparing a series of novel indazole analogs that are selective inhibitors of phosphodiesterase (PDE) type IV and the production of tumor necrosis factor (TNF), and as such are useful in the treatment of asthma, arthritis, bronchitis, chronic obstructive airway disease, psoriasis, allergic rhinitis, dermatitis, and other inflammatory diseases, AIDS, septic shock and other diseases involving the production of TNF.

Since the recognition that cyclic adenosine phosphate (AMP) is an intracellular second messenger, E. W. Sutherland, and T. W. Rall, Pharmacol. Rev., 12, 265, (1960), inhibition of the phosphodiesterases has been a target for modulation and, accordingly, therapeutic intervention in a range of disease processes. More recently, distinct classes of PDE have been recognized, J. A. Beavo et al., TiPS, 11, 150, (1990), and their selective inhibition has led to improved drug therapy, C. D. Nicholson, M. S. Hahid, TiPS, 12, 19, (1991). More particularly, it has been recognized that inhibition of PDE type IV can lead to inhibition of inflammatory mediator release, M. W. Verghese et al., J. Mol. Cell Cardiol., 12 (Suppl. II), S 61, (1989) and airway smooth muscle relaxation (T. J. Torphy in "Directions for New Anti-Asthma Drugs," eds. S. R. O'Donnell and C. G. A. Persson, 1988, 37 Birkhauser-Verlag). Thus, compounds that selectively inhibit PDE type IV by exhibiting low levels of activity against other PDE receptor types, inhibit the release of inflammatory mediators and relax airway smooth muscle without causing cardiovascular effects or antiplatelet effects.

An especially useful class of selective PDE4 inhibitors is that disclosed in U.S. application Ser. No. 08/963904, filed Apr. 1, 1997 (Attorney Docket No. PC9281B), which is a continuation-in-part of U.S. provisional application Ser. No. 60/016861, filed May 3, 1996 (Attorney Docket No. 9281), now abandoned; and in international application Ser. No. PCT/IB97/00323 based on said provisional application, filed Apr. 1, 1997 (Attorney Docket No. PC9281A), designating the United Sates, and published as WO 97/42174 on Nov. 13, 1997. Both of said applications are incorporated herein by reference in their entireties.

The class of selective PDE4 inhibitors disclosed in the above-mentioned applications may be prepared in accordance with the synthesis procedures described in U.S. provisional application Ser. No. 60/046858, filed May 8, 1997 (Attorney Docket No. 9798), now abandoned; and in international application Ser. No. PCT/IB98/00647 based on said provisional application, filed Apr. 28, 1998 (Attorney Docket No. PC9798A), designating the United Sates, and published as WO 98/*** on November , 1998. Both of said applications are incorporated herein by reference in their entireties for their disclosure of the state of the art with respect to preparation of indazole carboxylic acid PDE4 inhibitors. However, there is no suggestion therein of the preparation process of the present invention.

The above-mentioned class of indazole carboxylic acid selective PDE4 inhibitors comprises compounds of Formula (II):

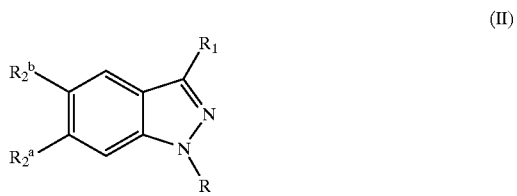

(II)

and pharmaceutically acceptable salts thereof, wherein
R is hydrogen, $(C_1-C_6)$ alkyl, $(-CH_2)_n(C_3-C_7)$ cycloalkyl wherein n is 0 to 2, or $-(Z')_b(C_6-C_{10})$ aryl wherein b is independently 0 or 1, and Z' is $(C_1-C_6)$ alkylene or $(C_2-C_6)$-alkenylene, and wherein said alkyl and aryl moieties of said R groups are optionally substituted by one or more substituents independently selected from halo, hydroxy, $(C_1-C_5)$ alkyl, $(C_1-C_5)$ alkoxy, or trifluoromethyl;
$R_1$ is hydrogen, $(C_1-C_7)$ alkyl, phenyl, or $(C_3-C_7)$ cycloalkyl, wherein said alkyl and phenyl $R_1$ groups are optionally substituted with up to 3 substituents independently selected from the group consisting of methyl, ethyl, trifluoromethyl, and halo; and
$R_2^a$ and $R_2^b$ are independently selected from the group consisting essentially of hydrogen and recited substituents, provided that one, but not both of $R_2^a$ and $R_2^b$ must be independently selected as hydrogen, wherein said substituents comprise, among others those of Formula (IIa):

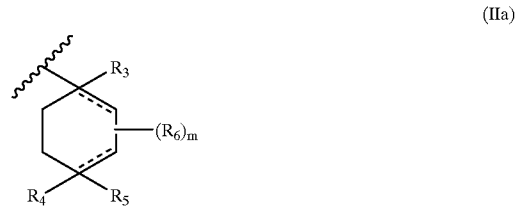

(IIa)

wherein the dashed lines in formula (Ia) independently and optionally represent a single or double bond, provided that in formula (Ia) both dashed lines cannot both represent double bonds at the same time.

Within the above-described class of PDE4 inhibitors, is a group of especially active compounds in which $R_2$, which includes and refers to "$R_2^a$" and "$R_2^b$", is a group of formula (Ia) wherein the dashed line attached to the ring carbon atom to which $R_3$ is attached represents a single bond, m is 0, $R_5$ is hydrogen and $R_4$ is $-OH$, $-CH_2OH$, $-C(CH_3)_2OH$, $-CO_2H$, $-CO_2CH_3$, $-CO_2CH_2CH_3$, or $-CH_2C(O)NH_2$. Further of particular interest within the above-described group of compounds are those wherein $R_3$ is cyano, $R_4$ is —$CO_2H$, R is cyclohexyl, cyclopentyl, cyclobutyl, methylenecyclopropyl, isopropyl, phenyl or 4-fluorophenyl, and particularly wherein R is cyclohexyl; and $R_1$ is ($C_1$–$C_2$) alkyl optionally substituted by up to three fluorines, and particularly wherein $R_1$ is ethyl. It is also important among the above-described group of compounds that $R_3$ and $R_5$ are cis as represented in Formula (IIb):

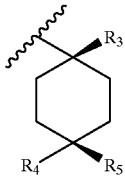
(IIb)

Among the most preferred species of compounds as above-described are the following:

Cis-4-cyano-4-(1-cyclohexyl-3-ethyl-1H-indazol-6-yl) cyclohexanecarboxylic acid; and Cis-4-cyano-4-(1-cyclohexyl-3-ethyl-1H-indazol-6-yl) cyclohexanecarboxylic acid methyl ester.

The above-identified preferred compounds may be represented by Formulas (IIc) and (IId):

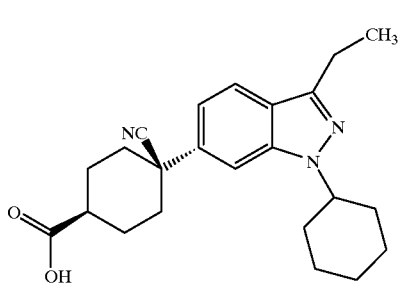
(IIc)

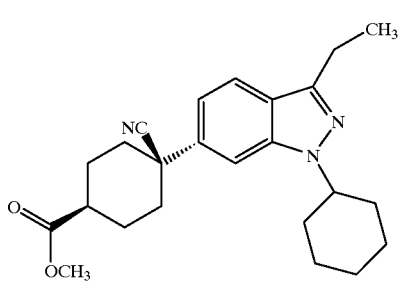
(IId)

SUMMARY OF THE INVENTION

The present invention relates to a method of preparing a compound of Formula (I):

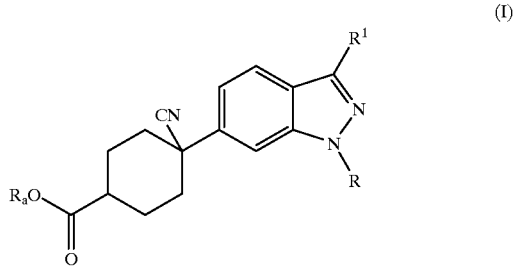
(I)

wherein $R_a$ is selected from the group consisting essentially of hydrogen; ($C_1$–$C_6$) alkyl; and phenyl and ($C_1$–$C_3$) alkyl-phenyl wherein said phenyl groups are optionally substituted by one or two substituents selected from the group consisting essentially of —($C_1$–$C_4$) alkyl; —O($C_1$–$C_3$) alkyl; Br; and Cl;

R is selected from the group consisting essentially of hydrogen; ($C_1$–$C_6$) alkyl; —$(CH_2)_n$($C_3$–$C_7$) cycloalkyl wherein n is 0 to 2; and —$(Z')_b$($C_6$–$C_{10}$) aryl wherein b is independently 0 or 1, and Z' is ($C_1$–$C_6$) alkylene or ($C_2$–$C_6$) alkenylene; wherein said alkyl and aryl moieties of said R groups are optionally substituted by one or more substituents independently selected from the group consisting essentially of halo, preferably F or Cl; hydroxy; ($C_1$–$C_5$) alkyl; ($C_1$–$C_5$) alkoxy; and trifluoromethyl; and $R^1$ is selected from the group consisting essentially of hydrogen; ($C_1$–$C_6$) alkyl; phenyl; and ($C_3$–$C_7$) cycloalkyl; wherein said alkyl and phenyl $R^1$ groups are optionally substituted with up to 3 substituents independently selected from the group consisting essentially of methyl, ethyl, trifluoromethyl, and halo;

comprising:

(a) treating a compound of Formula (Ia):

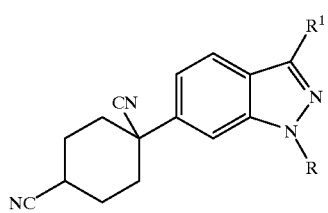
(Ia)

wherein R and $R^1$ are as defined above, with an alcohol comprising a compound of Formula (Ib-A) and an acid comprising a compound of Formula (Ib-B):

$R_a$—OH   and   HX
(Ib-A)         (Ib-B)

where $R_a$ is as defined above; and HX is an acid selected from the group consisting essentially of hydrobromic acid; hydrochloric acid; sulfuric acid; sulfonic acid; and aliphatic and aromatic sulfonic acids selected from the group consisting essentially of methanesulfonic acid, trifluoromethanesulfonic acid, benzenesulfonic acid, benzylsulfonic acid, p-toluene sulfonic acid, and camphorsulfonic acid, whereby HX provides the acidic conditions which result in formation of a salt of the corresponding imidate of Formula (Ic):

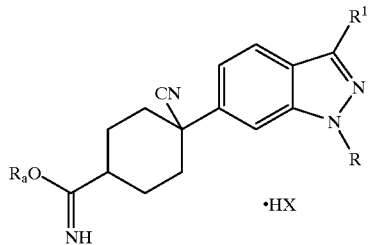

(Ic)

and (b) hydrolyzing said compound of Formula (Ic) to provide said compound of Formula (I).

The present invention further relates to the above-defined method of preparation wherein $R_a$ is selected from the group consisting essentially of hydrogen; ($C_1$–$C_6$) alkyl; and phenyl and benzyl wherein said phenyl and benzyl groups are optionally substituted by one or two substituents selected from the group consisting essentially of methyl, ethyl, iso-propyl, methoxy, Br and Cl; R is selected from the group consisting essentially of cyclohexyl, cyclopentyl, cyclobutyl, methylene-cyclopropyl, isopropyl, phenyl or 4-fluoro-phenyl, and particularly wherein R is cyclohexyl; and wherein $R^1$ is selected from the group consisting essentially of ($C_1$–$C_2$) alkyl optionally substituted by up to three fluorines, and particularly wherein $R^1$ is ethyl. Also further in accordance with the present invention there is provided said method of preparation wherein said compound of Formula (I) is cis-4-cyano-4-(1-cyclohexyl-3-ethyl-1H-indazol-6-yl)cyclohexanecarboxylic acid ethyl ester.

Still further, the present invention relates to a method of preparing a compound of Formula (I):

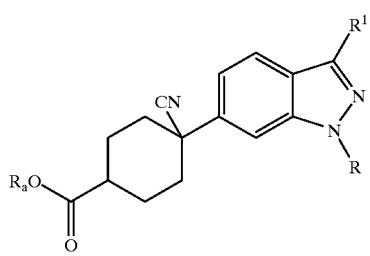

(I)

wherein $R_a$, R and $R^1$ are as defined further above; comprising:

(a) treating a compound of Formula (Id):

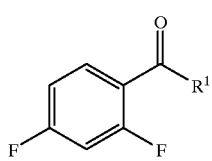

(Id)

wherein $R^1$ is as defined above with a hydrazine of Formula (Ie):

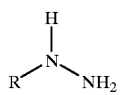

(Ie)

wherein R is as defined above, to provide a compound of Formula (If)

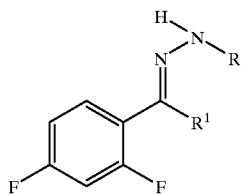

(If)

wherein R and $R^1$ are as defined above, followed by (b) heating said compound of Formula (If) to provide an indazole of Formula (Ig):

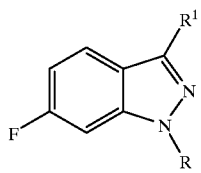

(Ig)

wherein R and $R^1$ are as defined above, followed by (c) treating said indazole of Formula (Ig) with cyclohexane-1,4-dicarbonitrile of Formula (Ih):

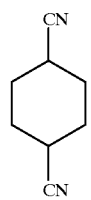

(Ih)

to provide a compound of Formula (Ia)

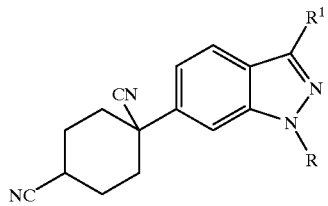

(Ia)

wherein R and $R^1$ are as defined above; followed by (d) treating said compound of Formula (Ia) with an alcohol comprising a compound of Formula (Ib-A) and an acid comprising a compound of Formula (Ib-B):

$R_a$—OH  and  HX
(Ib-A)         (Ib-B)

wherein $R_a$ is as defined above; and HX is an acid selected from the group consisting essentially of hydrobromic acid; hydrochloric acid; sulfuric acid; sulfonic acid; and aliphatic and aromatic sulfonic acids selected from the group consisting essentially of methanesulfonic acid, trifluoromethanesulfonic acid, benzenesulfonic acid, benzylsulfonic acid, p-toluene sulfonic acid, and camphorsulfonic acid, whereby HX provides the acidic conditions which result in formation of a salt of the corresponding imidate of Formula (Ic):

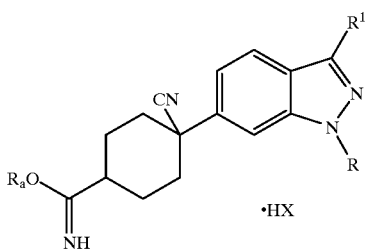
(Ic)

and (e) hydrolyzing said compound of Formula (Ic) to provide said compound of Formula (I).

Yet further, the present invention relates to the above-defined method of preparation wherein R is cyclohexyl, cyclopentyl, cyclobutyl, methylene-cyclopropyl, isopropyl, phenyl or 4-fluoro-phenyl, and particularly wherein R is cyclohexyl; and wherein $R^1$ is $(C_1-C_2)$ alkyl optionally substituted by up to three fluorines, and particularly wherein $R^1$ is ethyl.

Also further in accordance with the present invention there is provided said method of preparation wherein said compound of Formula (I) is cis-4-cyano-4-(1-cyclohexyl-3-ethyl-1H-indazol-6-yl)cyclohexanecarboxylic acid ethyl ester.

The present invention still further relates to a method of facilitating the handling and purification of free base indazole intermediates of Formula (Ig):

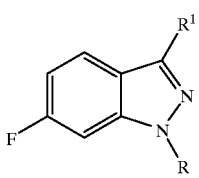
(Ig)

wherein R and $R^1$ are as defined further above, comprising:

(a) treating said free base indazole of Formula (Ig) with an acid selected from the group consisting essentially of hydrobromic acid; hydrochloric acid; sulfuric acid; sulfonic acid; and aliphatic and aromatic sulfonic acids selected from the group consisting essentially of methanesulfonic acid, trifluoromethanesulfonic acid, benzenesulfonic acid, benzylsulfonic acid, p-toluene sulfonic acid, and camphorsulfonic acid, to form a salt of the compound of Formula (Ig²):

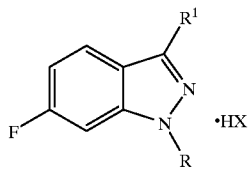
(Ig²)

wherein HX is as defined above and indicates the acid used to prepare the salt, with X being the anion of said acid;

(b) separating and purifying said salt of Formula (Ig²); followed by:

(c) converting said salt of Formula (Ig²) back to said free base indazole of Formula (Ig) by treating it with an aqueous base selected from the group consisting essentially of sodium hydroxide, potassium hydroxide, sodium carbonate, sodium bicarbonate, potassium carbonate, and potassium bicarbonate, preferably sodium hydroxide, to provide said compound of Formula (Ig).

The present invention also concerns novel intermediates useful in the above-described methods of preparing compounds of Formula (I). The first group of said novel intermediates is a subclass of the intermediates of Formula (If) recited above, represented by Formula (If²):

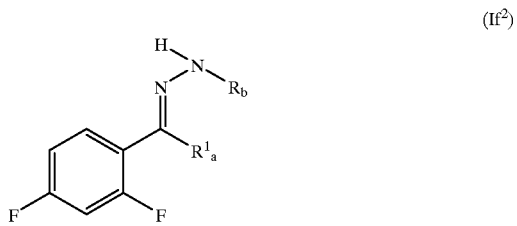
(If²)

wherein $R_b$ is selected from the group consisting essentially of $(C_3-C_7)$ cycloalkyl and phenyl optionally substituted by one or more substituents independently selected from halo, hydroxy, $(C_1-C_5)$ alkyl, $(C_1-C_5)$ alkoxy, and trifluoromethyl; and $R^1_a$ is selected from the group consisting essentially of $(C_1-C_6)$ alkyl optionally substituted with up to 3 substituents independently selected from the group consisting essentially of trifluoromethyl, fluoro and chloro.

In preferred embodiments, $R_b$ is cyclohexyl, cyclopentyl, cyclobutyl, phenyl or 4-fluoro-phenyl, and $R^1_a$ is $(C_1-C_2)$ alkyl optionally substituted by up to three fluorines. In the most preferred embodiments $R_b$ is cyclohexyl and $R^1_a$ is ethyl.

The present invention further concerns the above-mentioned second group of novel intermediates useful in the above-described methods of preparing compounds of Formula (I). Said second group of novel intermediates is essentially the class of intermediates of Formula (Ic) recited above, but further including the recited compounds which are not in the form of "HX" salts as defined. This second group of novel intermediates is accordingly represented by Formula (Ic²):

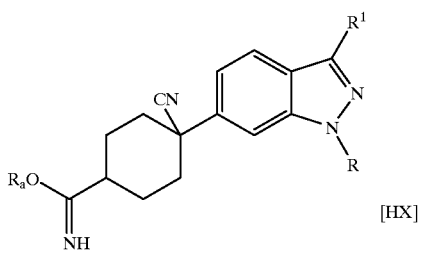

wherein
- $R_a$ is selected from the group consisting essentially of hydrogen; $(C_1-C_6)$ alkyl; and phenyl and $(C_1-C_3)$ alkyl-phenyl wherein said phenyl groups are optionally substituted by one or two substituents selected from the group consisting essentially of —$(C_1-C_4)$ alkyl; —$O(C_1-C_3)$ alkyl; Br; and Cl;
- R is selected from the group consisting essentially of hydrogen; $(C_1-C_6)$ alkyl; —$(CH_2)_n(C_3-C_7)$ cycloalkyl wherein n is 0 to 2; and —$(Z')_b(C_6-C_{10})$ aryl wherein b is independently 0 or 1; and Z' is $(C_1-C_6)$ alkylene or $(C_2-C_6)$ alkenylene; wherein said alkyl and aryl moieties optionally substituted by one or more substituents independently selected from the group consisting essentially of halo, preferably F or Cl, hydroxy, $(C_1-C_5)$ alkyl, $(C_1-C_5)$ alkoxy, or trifluoromethyl;
- $R^1$ is selected from the group consisting essentially of hydrogen; $(C_1-C_6)$ alkyl; phenyl; and $(C_3-C_7)$ cycloalkyl; wherein said alkyl and phenyl groups are optionally substituted with up to 3 substituents independently selected from the group consisting essentially of methyl, ethyl, trifluoromethyl, and halo; and
- [HX] represents an optional salt formed with the basic imino group of the (Ic$^2$) compound by treatment thereof with an acid selected from the group consisting essentially of hydrochloric acid; hydrobromic acid; sulfuric acid; sulfonic acid, and aliphatic and aromatic sulfonic acids selected from the group consisting essentially of methanesulfonic acid, trifluoromethanesulfonic acid, benzenesulfonic acid, benzylsulfonic acid, p-toluenesulfonic acid, and camphorsulfonic acid; preferably hydrochloric acid, In preferred embodiments of the intermediates of Formula (Ic$^2$), $R_a$ is selected from the group consisting essentially of hydrogen; $(C_1-C_6)$ alkyl; and phenyl and benzyl wherein said phenyl and benzyl groups are optionally substituted by one or two substituents selected from the group consisting essentially of methyl, ethyl, iso-propyl, methoxy, Br and Cl; R is selected from the group consisting essentially of $(C_3-C_7)$ cycloalkyl and phenyl optionally substituted by one or more substituents independently selected from halo, hydroxy, $(C_1-C_5)$ alkyl, $(C_1-C_5)$ alkoxy, and trifluoromethyl; $R^1$ is selected from the group consisting essentially of $(C_1-C_6)$ alkyl optionally substituted with up to 3 substituents independently selected from the group consisting essentially of trifluoromethyl, fluoro and chloro; and [HX] represents a salt of hydrobromic or hydrochloric acid.

In more preferred embodiments of the intermediates of Formula (Ic$^2$), $R_a$ is selected from the group consisting essentially of hydrogen; ethyl, propyl, iso-propyl; phenyl; benzyl; 3,5-dimethylphenyl and 3,5-dimethylbenzyl; 4-iso-propylphenyl and 4-iso-propylbenzyl; and 4-bromophenyl and 4-bromobenzyl; R is cyclohexyl, cyclopentyl, cyclobutyl, phenyl or 4-fluoro-phenyl; $R^1$ is $(C_1-C_2)$ alkyl optionally substituted by up to three fluorines; and [HX] represents a salt of hydrochloric acid. In the most preferred embodiments of the intermediates of Formula (Ic$^2$), $R_a$ is hydrogen, ethyl, propyl, iso-propyl benzyl, 4-iso-propylphenyl, or 4-bromobenzyl; R is cyclohexyl; $R^1$ is ethyl; and [HX] represents a salt of hydrochloric acid.

DETAILED DESCRIPTION OF THE INVENTION

A generalized representation of the herein described methods of preparing said compounds of Formula (I) as defined further above, is illustrated and described immediately below in the schematic synthesis diagram and corresponding explanation designated as Scheme (I):

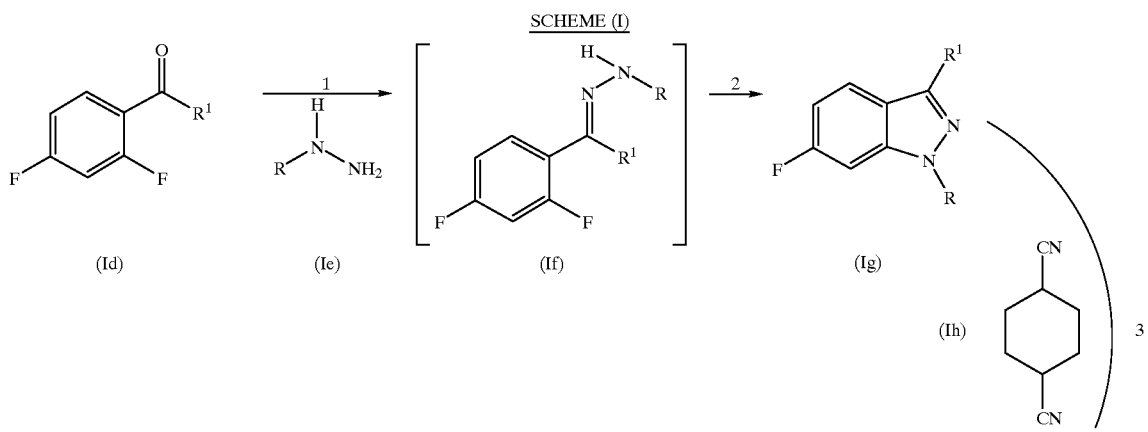

-continued

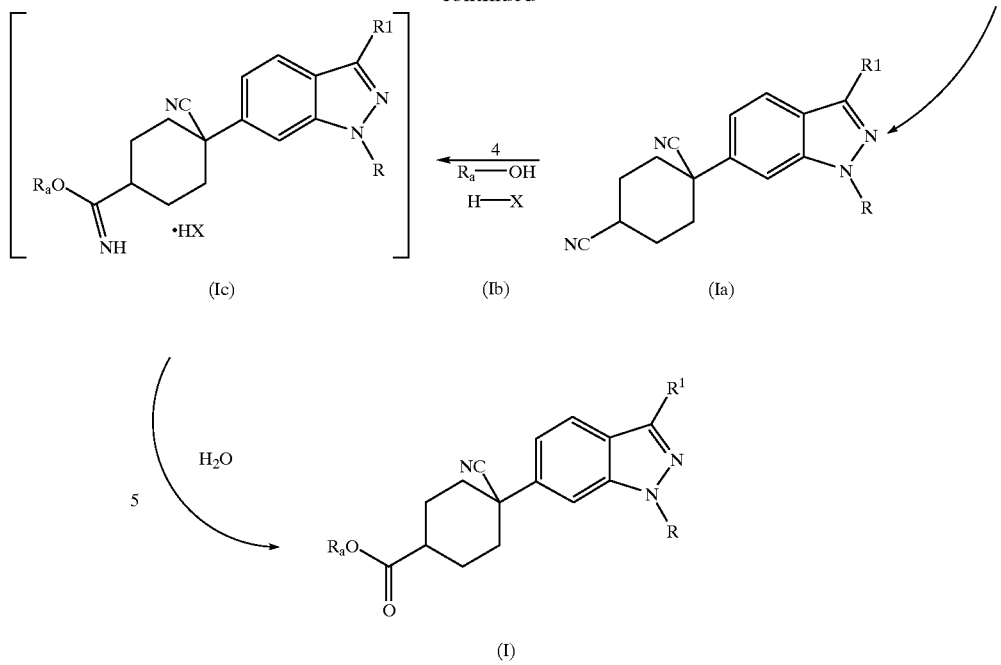

As illustrated, the starting material (Id) is reacted with a hydrazine (Ie) and the in situ product (If) is heated without separation to yield an indazole (Ig), which is in turn reacted with dicyanocyclohexane (Ih) to yield the cyano- analog of said above-described preferred compound, (Ic).

In Step 1 of Scheme (I), the compound of Formula (Id) is treated with a hydrazine derivative of Formula (Ie) and an acid, preferably ammonium acetate, in a solvent such as heptane, tetrahydrofuran, xylenes, toluene, or mesitylene, or a mixture of two or more of the foregoing solvents, preferably toluene, to provide the compound of Formula (If). The formation of the intermediate compound of Formula (If) has been observed by HPLC, but in general, the compound of Formula (If) need not, and is usually not separated or isolated from the reaction mixture. Accordingly, where the reaction mixture proceeds in situ on to Step 2, it will be subjected to heating at temperatures of about 75° C. to about 200° C. in order to accomplish indazole ring formation.

However, should it be desired to isolate the intermediate compound of Formula (If), the reaction mixture in Step 1 will be heated to from about 20° C. to about 90° C.

In Step 2 of Scheme (I), the reaction mixture containing the compound of Formula (If) is heated at a temperature between about 75° C. and about 200° C., preferably between about 90° and 120° C., for a period of about 2 hours to 48 hours, preferably 12 hours, to provide the compound of formula (Ig). The indazole nucleus of the compounds of Formula (I) is thus created by ring formation from the intermediate of Formula (If). It will be noted that said ring formation maintains the arrangement of the R and $R^1$ substituents, which may be illustrated by the following partial reaction Scheme (IA) which uses preferred definitions of R and $R^1$ to show Steps 1 and 2 of Scheme (I):

SCHEME (IA)

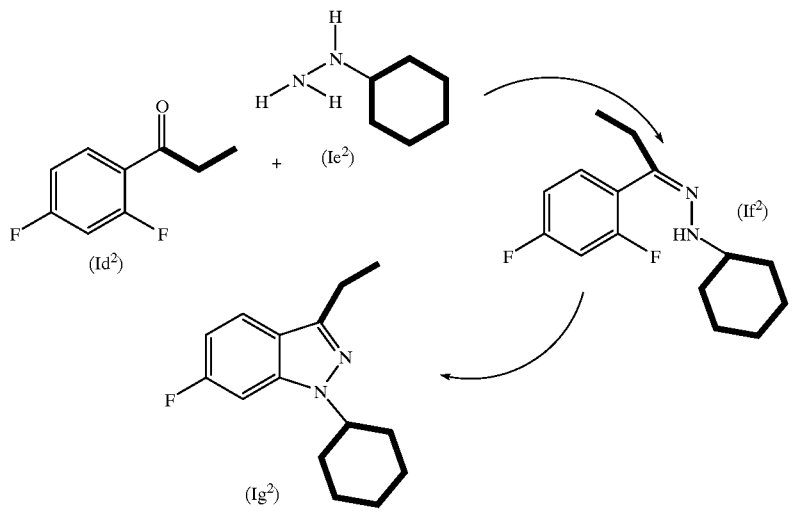

Alternatively, the process of Step 1 of Scheme (I) may be accomplished using a salt of the hydrazine derivative, such as the hydrochloride; hydrobromide; methylsulfonate, i.e., mesylate (MsOH); tosylate; or oxalate salt of said compound, preferably the mesylate salt, which is reacted with a base, such as sodium or potassium acetate, in a solvent such as heptane, tetrahydrofuran, xylenes, toluene, or mesitylene, or a mixture of two or more of the foregoing solvents, preferably toluene.

In Step 3 of Scheme (I), the compound of Formula (Ig) is treated with the compound of Formula (Ih) in the presence of a base such as lithium bis(trimethylsilyl)amide, sodium bis(trimethylsilyl)amide, potassium bis(trimethylsilyl) amide (KHMDS), lithium diisopropylamide, or lithium 2,2, 6,6-tetramethylpiperidine. These bases are selective and permit acceptably high levels of addition of the cyclohexane-1,4-dicarbonitrile (Ih) to the R- and $R^1$-substituted indazole (Ig) by displacement of the fluorine atom on the latter, while retaining both carbonitrile functionalities in place. Preferably, potassium bis(trimethylsilyl) amide (KHMDS) is used, in a solvent such as tetrahydrofuran, toluene, or xylenes, preferably toluene, at a temperature between about 25° C. and about 125° C., preferably about 100° C., for a period of from 1 hour to 15 hours, preferably about 5 hours, to provide a compound of Formula (Ia).

In Step 4 of Scheme (I), the compound of Formula (Ia) is treated with an acid such as hydrochloric acid, hydrobromic acid, sulfuric acid, p-toluenesulfonic acid, methanesulfonic acid, or trifluoromethanesulfonic acid, preferably hydrochloric acid, in a solvent/reactant of Formula (Ib), i.e., $R_a$—OH wherein $R_a$ is as defined herein, e.g., ($C_1$-$C_6$) alkyl, such as methanol, ethanol, propanol, iso-propanol, preferably ethanol, at a temperature between 0° C. and 50° C., preferably ambient temperature (20°–25° C.) for a period of from 1 hour to 48 hours, preferably about 14 hours, to provide a compound of Formula (Ic). In general, the compound of Formula (Ic) need not to be separated or isolated from the reaction mixture.

In Step 5 of Scheme (I), the compound of Formula (Ic) is treated with water (hydrolyzed) in a solvent such as toluene, ethyl acetate, diisopropyl ether, methyl tert-butyl ether, or dichloromethane, preferably toluene, at a temperature between about 0° C. and 50° C., preferably ambient temperature (20°–25° C.) for a period of 1 hour to 24 hours, preferably 8 hours, to provide a compound of Formula (I).

A particular version of the synthesis of Scheme (I) above carried out with reactants suitable for obtaining the preferred ethyl ester protected cyclohexanecarboxylic acid compound, is illustrated below in Scheme (II):

SCHEME (II)

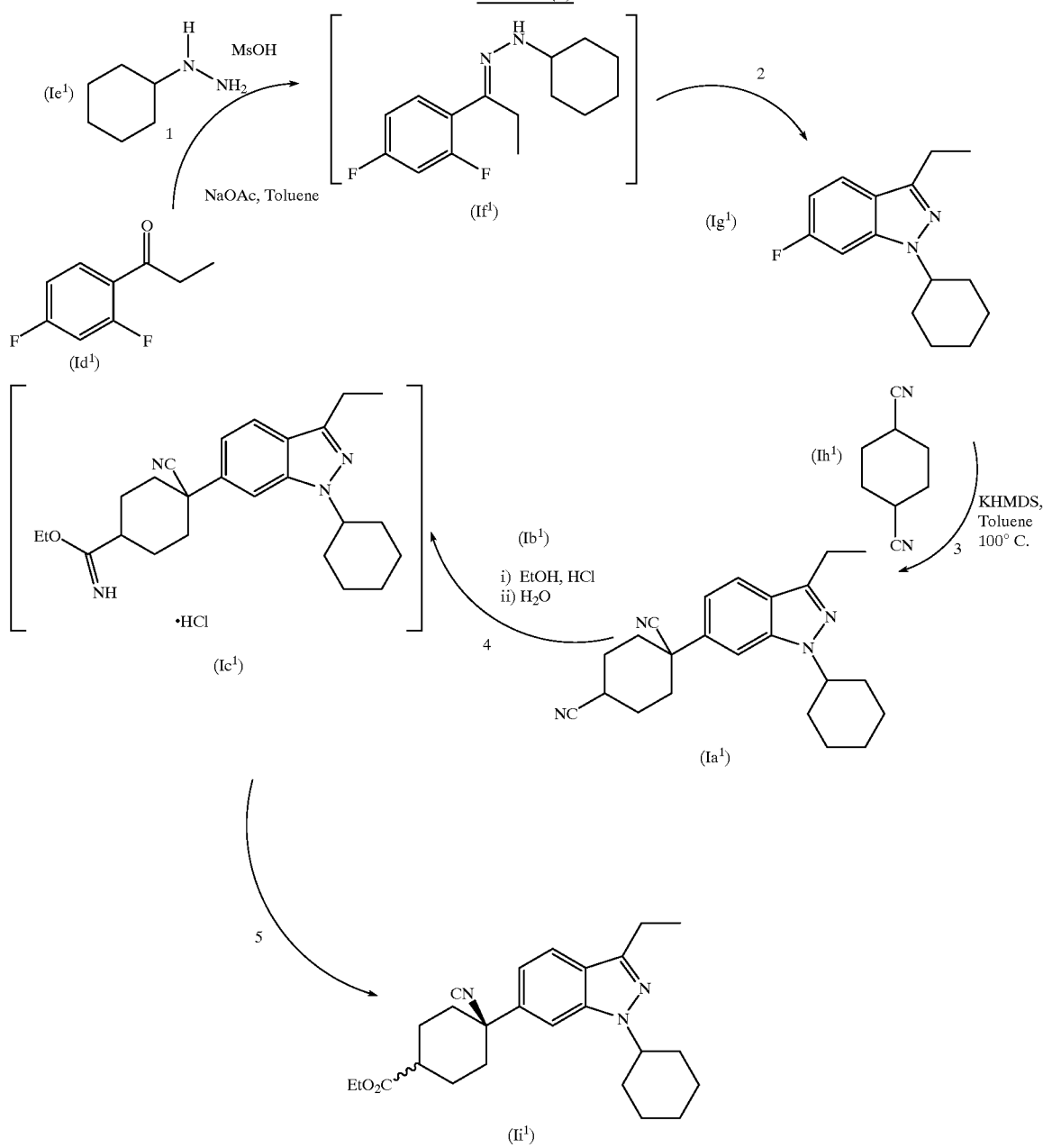

Scheme (III) set out below illustrates a procedure to facilitate the handling and purification of the indazole intermediate of Formula (Ig) which is described above with reference to Scheme (I). In Step 1 of Scheme (III), the indazole of formula (Ig) is treated with an acid selected from the group consisting essentially of hydrobromic acid; hydrochloric acid; sulfuric acid; sulfonic acid, and aliphatic and aromatic sulfonic acids selected from the group consisting essentially of methanesulfonic acid, trifluoromethanesulfonic acid, benzenesulfonic acid, benzylsulfonic acid, p-toluene sulfonic acid, and camphorsulfonic acid, preferably hydrobromic acid; in a solvent such as toluene, xylenes, acetic acid, or ethyl acetate, preferably toluene, at a temperature ranging from 0° C. to ambient temperature (20°–25° C.), preferably ambient temperature, to form a salt of the compound of Formula (1g$^2$), wherein HX is as defined herein and indicates the acid used to prepare the salt, X being the anion of said acid. The salt may be separated and purified according to methods familiar to those skilled in the art. In Step 2 of Scheme (III), the salt is converted back to the free base. In this step, the salt of the compound of Formula (Ig2) is treated with an aqueous base, such as sodium hydroxide, potassium hydroxide, sodium carbonate, sodium bicarbonate, potassium carbonate, or potassium bicarbonate, preferably sodium hydroxide, in a solvent such as hexane, toluene, dichloromethane, diisopropyl ether, methyl tert-butyl ether, or ethyl acetate, preferably toluene, at a temperature ranging from 0° C. to ambient temperature (20°–25° C.), preferably ambient temperature, for a period of 5 minutes to 1 hour, preferably about 20 minutes, to provide the compound of Formula (Ig).

SCHEME (III)

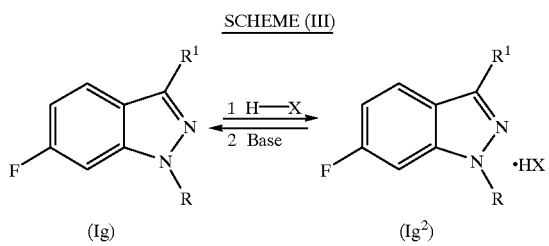

The compounds of Formulas (I)–(Ii$^1$) may have asymmetric carbon atoms and therefore exist in different enantiomeric forms. Diastereomeric mixtures can be separated into their individual diastereomers on the basis of their physical chemical differences by methods known to those skilled in the art, for example, by chromatography or fractional crystallization. Enantiomers may be separated by converting the enantiomeric mixtures into a diastereomeric mixture by reaction with an appropriate optically active compound, e.g., alcohol, separating the diastereomers and converting, e.g., hydrolyzing, the individual diastereomers to the corresponding pure enantiomers. The use of all such isomers, including diastereomer mixtures and pure enantiomers, are considered to be part of the present invention.

The compounds of Formulas (I)–(Ii$^1$) that are basic in nature are capable of forming a wide variety of different salts with various inorganic and organic acids. Although such salts must be pharmaceutically acceptable for administration to mammals, it is often desirable in practice to initially isolate the compound of Formula (I)–(Ii$^1$) from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired salt can also be precipitated from a solution of the free base in an organic solvent by adding to the solution an appropriate mineral or organic acid.

Those compounds of Formulas (I)–(Ii$^1$) that are acidic in nature are capable of forming base salts with various cations. For compounds that are to be administered to mammals, such salts must be pharmaceutically acceptable. Where a pharmaceutically acceptable salt is required, it may be desirable to initially isolate the compound of Formula (I)–(Ii$^1$) from the reaction mixture as a pharmaceutically unacceptable salt and then simply convert the latter to a pharmaceutically acceptable salt in a process analogous to that described above relating to the conversion of pharmaceutically unacceptable acid addition salts to pharmaceutically acceptable salts. Examples of base salts include the alkali metal or alkaline-earth metal salts and particularly the sodium, amine, and potassium salts. These salts are all prepared by conventional techniques.

The chemical bases which are used as reagents to prepared the pharmaceutically acceptable base salts of this invention are those which form non-toxic base salts with the acidic compounds of Formulas (I)–(Ii$^1$). Such non-toxic base salts include those described from such pharmacologically acceptable cations as sodium, potassium, calcium, magnesium, various amine cations, etc., and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

DESCRIPTION OF PREFERRED EMBODIMENTS

The following Examples further illustrate the method and intermediates of the present invention. It will be understood that there is no intention to limit the present invention to the specific details of the Examples provided below, but rather that the claims appended hereto should be the basis for any recitation or delineation of the present invention.

EXAMPLE 1

1-Cyclohexyl-3-ethyl-6-fluoro-1H-indazole

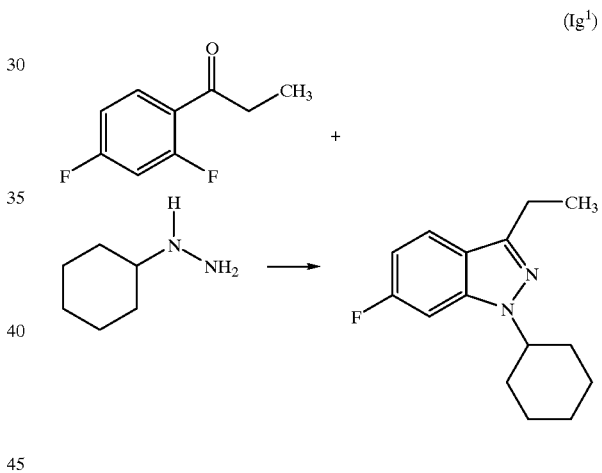

To a solution of 1-(2,4-difluoro-phenyl)-propan-1-one (21.29 g, 125.1 mmol) in toluene (120 mL) was added sodium acetate (26.75 g, 326.1 mmol) and cyclohexylhydrazine mesylate (34.0 g, 163 mmol). The reaction mixture was heated to reflux in a Dean-Stark apparatus for 12 hours. The reaction was cooled to room temperature and poured into 1 N hydrochloric acid (100 mL). The toluene layer was separated and washed with water (75 mL) and brine (75 mL). The organic layer was dried over magnesium sulfate, filtered, and concentrated to yield 30.07 g of 1-cyclohexyl-3-ethyl-6-fluoro-1H-indazole (98% yield). $^1$H NMR (400 MHz, CDCl$_3$) d 1.33 (t, 3, J=7.7), 1.35–1.44 (m, 2), 1.47–1.96 (m, 8), 2.93 (q, 2, J=7.7), 4.14–4.22 (m, 1), 6.81 (dt, 1, J=8.9, 2.1), 6.99 (dd, 1, J=9.8, 2.1), 7.40 (ddd, 1, J=8.7, 5.2, 0.4). $^{13}$C NMR (100 MHz, CDCl$_3$) d 13.97, 20.53, 25.37, 25.84, 32.32, 58.18, 94.77 (d, J=27.4), 109.11 (d, J=26.0), 119.38, 121.75 (d, J=11.5), 139.89 (d, J=13.0), 146.61, 161.95 (d, J=242).

IR 2968, 2934, 2856, 1624, 1507, 1174, 1125, 825 cm$^{-1}$. Analysis calculated for C$_{15}$H$_{19}$FN$_2$: C, 73.14; H, 7.77; N, 11.37. Found: C, 73.33; H, 7.90; N, 11.46.

EXAMPLE 2

1-(1-Cyclohexyl-3-ethyl-1H-indazol-6-yl)-cyclohexane-1,4-dicarbonitrile

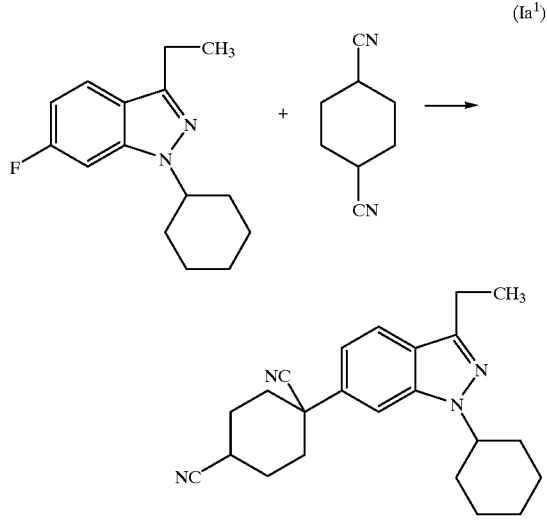

ethylacetate (1.69 g product isolated, 77% yield). Higher Rf diastereoisomer: $^1$H NMR (400 MHz, CDCl$_3$) d 1.37 (t, 3, J=7.7), 1.24–1.78 (m, 4), 1.92–2.10 (m, 6), 2.19–2.35 (m, 8), 2.98 (q, 2, J=7.7), 3.15–3.17 (m, 1), 4.30–4.39 (m, 1), 7.19 (dd, 1, J=8.5, 1.7), 7.51 (d, 1, J=0.8), 7.71 (d, 1, J=8.5). $^{13}$C NMR (100 MHz, CDCl$_3$) d 14.07, 20.60, 25.34, 25.79, 25.92, 32.61, 33.36, 44.30, 57.66, 105.92, 117.04, 121.00, 121.52, 121.79, 122.09.137.33, 139.54, 146.41. IR 2934, 2239, 1620, 1448, 1435, 1238, 1049, 803 cm$^{-1}$. Analysis calculated for C$_{25}$H$_{28}$N$_4$: C, 76.63; H, 7.83; N, 15.54. Found: C, 76.69; H, 7.87; N, 15.65. Lower Rf diastereoisomer: $^1$H NMR (400 MHz, CDCl$_3$) d 1.36 (t, 3, J=7.7), 1.42–1.53 (m, 2), 1.74–1.82 (m, 2), 1.89–2.08 (m, 8), 2.17–2.34 (m, 6), 2.58 (tt, 1, J=12.2, 3.5), 2.97 (q, 2, J=7.7), 4.28–4.36 (m, 1), 7.09 (dd, 1, J=8.5, 1.7), 7.49 (d, 1, J=1.0), 7.69 (d, 1, J=8.5). $^{13}$C NMR (100 MHz, CDCl$_3$) d 14.02, 20.57, 25.32, 25.81, 27.07, 27.27, 32.57, 36.04, 43.63, 57.75, 106.05, 116.65, 121.17, 121.50, 122.13, 137.17, 139.54, 146.38. IR 2935, 2231, 1620, 1447, 1211, 1061, 807 cm$^{-1}$. Analysis calculated for C$_{25}$H$_{28}$N$_4$: C, 76.63; H, 7.83; N, 15.54. Found: C, 76.52; H, 7.95; N, 15.37.

EXAMPLE 3

4-Cyano-4-(1-cyclohexyl-3-ethyl-1H-indazol-6-yl)-cyclohexanecarboxylic acid ethyl ester

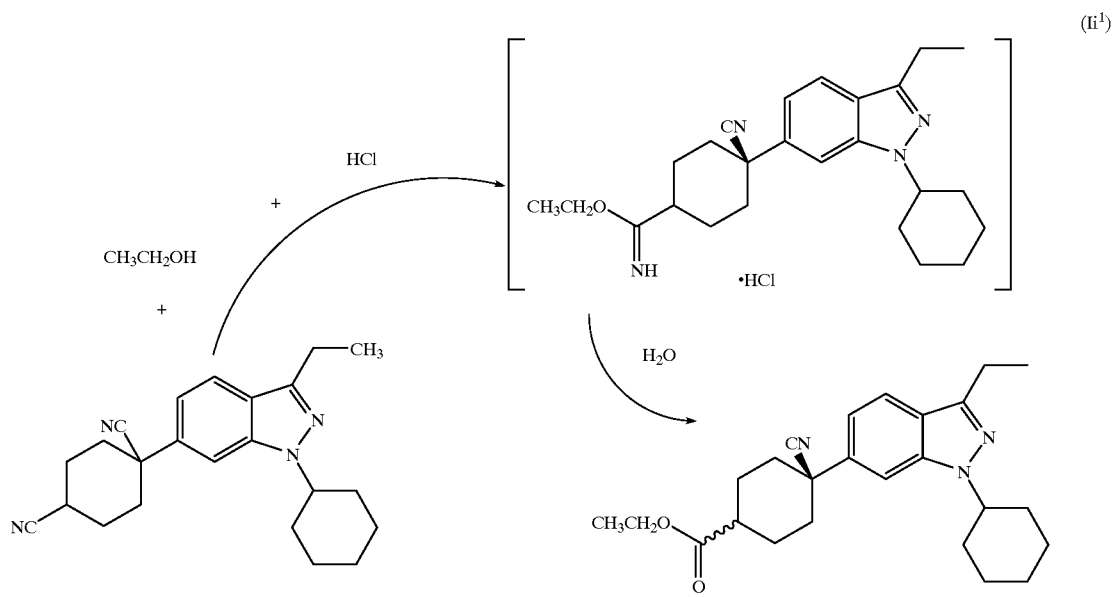

To a solution of 1-cyclohexyl-3-ethyl-6-fluoro-1H-indazole (1.509, 6.09 mmol) and cylohexane-1,4-dicarbonitrile (3.27 g, 24.4 mmol) in toluene (15 mL) was added potassium bis(trimethylsilyl) amide (1.82 g, 9.12 mmol). The reaction mixture was heated to 100° C. and stirred for 5 hours. The reaction mixture was cooled to room temperature and poured into 1N HCI (15 mL). The layers were separated and the organic extracts were concentrated. The crude product was stirred in 20% EtOAc/Hexanes (15 mL) for 20 minutes and the solids were filtered (1.1 g of cylohexane-1,4-dicarbonitrile recovered). The filtrate was concentrated to a crude oil. For characterization purposes, the diastereoisomers were obtained by purification by chromatography on silica gel (125 g) eluting with 2:1 hexanes/

To a solution of 1-(1-cyclohexyl-3-ethyl-1H-indazol-6-yl)-cyclohexane-1,4-dicarbo-nitrile (2.58 g, 7.16 mmol) in ethanol (35 mL) was bubbled hydrochloric acid gas for 20 minutes. The reaction mixture was stirred 20 minutes after which the solvent was concentrated. To the crude product was added toluene (20 mL) and water (20 mL) and the mixture was stirred for 8 hours. The layers were separated and the toluene layer was concentrated to a crude foam. For characterization purposes, the diastereoisomers were obtained by purification by chromatography on silica gel eluting with 4:1 hexanes/ethylacetate (2.37 g product isolated, 81% yield). Higher R$_f$ diastereoisomer: $^1$H NMR (400 MHz, CDCl$_3$) δ 1.28 (t, 3, J=7.1), 1.36 (t, 3, J=7.7), 1.43–1.56 (m, 2), 1.74–1.77 (m, 2), 1.93–2.10 (m, 10), 2.20–2.24 (m, 2), 2.31 (d, 2, j=12.9), 2.30 (tt, 1, J=12.2, 3.5), 2.95 (q, 2, J=7.1) 4.29–4.37 (m, 1), 7.13 (d, 1, J=8.5), 7.52 (s, 1), 7.68 (d, 1, J=8.5). $^{13}$C NMR (100 MHz, CDCl$_3$) δ 14.06, 14.23, 20.62, 25.35, 25.81, 26.20, 32.57, 36.77, 42.15, 44.27, 57.67, 60.63, 106.08, 116.96, 121.22, 121.95, 122.19, 138.23, 139.61, 146.31, 174.30. Analysis calculated for $C_{25}H_{33}BrN_3O_2$: C, 73.68; H, 8.15; N, 10.31. Found: C, 73.58; H, 8.28; N, 10.38. Lower $R_f$ diastereoisomer: mp 89–91° C. $^1$H NMR (400 MHz, CDCl$_3$) δ1.26 (t, 3, J=7.1), 1.33 (t, 3, J=7.7), 1.40–1.54 (m, 2), 1.71–1.78 (m, 2), 1.89–2.19 (m, 13), 2.23–2.31(m, 2), 2.94 (q, 2, J=7.7), 4.17 (q, 2, J=7.1), 4.26–4.33 (m, 1), 7.10 (d, 1, J=8.5), 7.47 (s, 1), 7.64 (d, 1, J=8.5). $^{13}$C NMR (100 MHz, CDCl$_3$) δ 14.07, 14.29, 24.71, 25.35, 25.80, 32.58, 33.74, 37.57, 44.26, 57.59, 60.59, 106.05, 117.26, 121.16, 121.85, 122.61, 138.42, 139.60, 146.27, 174.47. Analysis calculated for $C_{25}H_{33}BrN_3O_2$: C, 73.68; H, 8.15; N, 10.31. Found: C, 73.62; H, 8.53; N, 10.30.

EXAMPLE 4

1-Cyclohexyl-3-ethyl-6-fluoro-1H-indazole hydrobromide

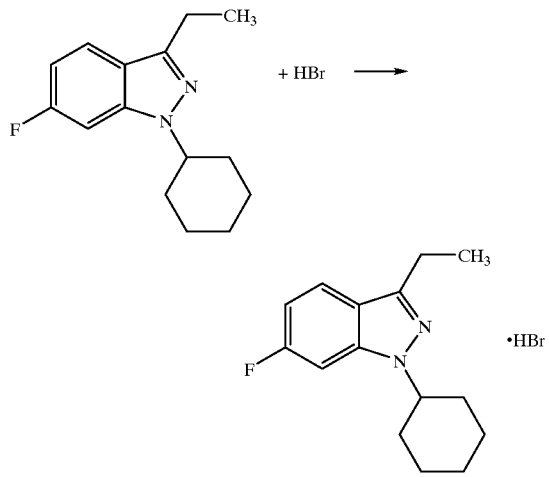

1-Cyclohexyl-3-ethyl-6-fluoro-1H-indazole (2.00 g, 8.12 mmol) was dissolved in toluene (20 mL) and to the solution was added hydrobromic acid (1.62 mL of a 30% solution in acetic acid). The solution was stirred at room temperature 30 minutes and concentrated to low volume. Ethyl acetate (10 mL) was added, the solids were filtered and washed with additional ethyl acetate (10 mL) to provide 1-cyclohexyl-3-ethyl-6-fluoro-1H-indazole hydrobromide (1.46 g, 55% yield) as an orange solid. $^1$H NMR (400 MHz, DMSO-d6) δ 1.22 (t, 3, J=7.7), 1.38–1.45 (m, 2), 1.60–1.83 (m, 8), 2.83 (q, 2, J=7.7), 4.36–4.43 (m, 1), 6.85–6.90 (m, 1), 7.47 (dd, 1, J=10.3, 1.7), 7.68 (dd, 1, J=8.8, 5.3). $^{13}$C NMR (100 MHz, DMSO-d6) δ 13.98, 20.26, 25.44, 25.49, 32.52, 56.80, 95.64 (d, J=27.5), 109.32 (d, J=26.0), 119.23, 122.38 (d, J=11.5), 140.02 (d, J=13.0), 146.11, 161.795 (d, J=241).

EXAMPLE 5

1-Cyclohexyl-3-ethyl-6-fluoro-1H-indazole

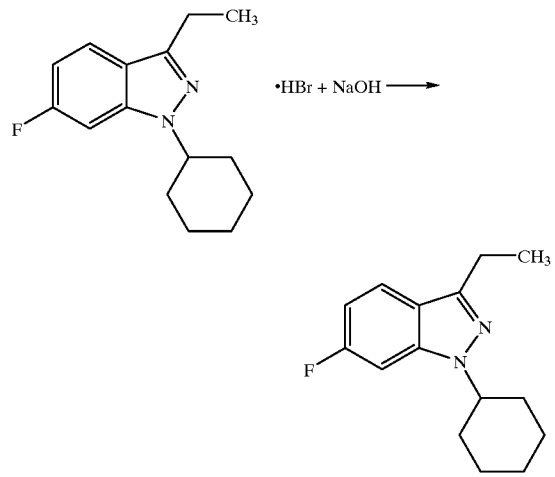

To 1-cyclohexyl-3-ethyl-6-fluoro-1H-indazole hydrobromide (0.440 g, 1.34 mmol) was added 1N aqueous sodium hydroxide (10 mL) and toluene (10 mL). The biphasic mixture was stirred for one hour and the layers were separated. The aqueous layer was reextracted with toluene (10 mL), and the organic extracts were combined, dried over magnesium sulfate, and concentrated to 1-cyclohexyl-3-ethyl-6-fluoro-1H-indazole (0.310 g, 94% yield). $^1$H NMR (400 MHz, CDCl$_3$) δ 1.33 (t, 3, J=7.7), 1.35–1.44 (m, 2), 1.47–1.96 (m, 8), 2.93 (q, 2, J=7.7), 4.14–4.22 (m, 1), 6.81 (dt, 1, J=8.9, 2.1), 6.99 (dd, 1, J=9.8, 2.1), 7.40 (ddd, 1, J=8.7, 5.2, 0.4). $^{13}$C NMR (100 MHz, CDCl$_3$) δ 13.97, 20.53, 25.37, 25.84, 32.32, 58.18, 94.77, (d, J=27.4), 109.11 (d, J=26.0), 119.38, 121.75 (d, J=11.5), 139.89 (d, J=13.0), 146.61, 161.95 (d, J=242).

What is claimed is:

1. A method of preparing a compound of Formula (I):

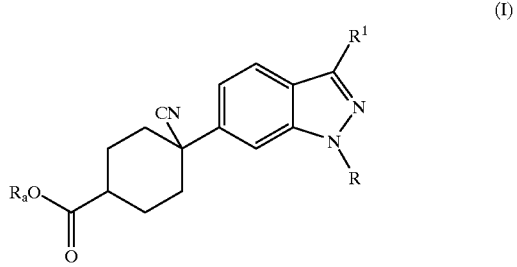

wherein $R_a$ is selected from the group consisting of hydrogen; ($C_1$–$C_6$) alkyl; phenyl and ($C_1$–$C_3$) alkyl-phenyl wherein said phenyl groups are unsubstituted or substituted with one or two substituents selected from the group consisting of —($C_1$–$C_4$) alkyl; —O($C_1$–$C_3$) alkyl; Br; and Cl;

R is selected from the group consisting of hydrogen; ($C_1$–$C_6$) alkyl; —($CH_2$)$_n$($C_3$–$C_7$) cycloalkyl where n is 0 to 2; and —(Z')$_b$($C_6$–$C_{10}$) aryl where b is independently 0 Z' is ($C_1$–$C_6$) alkylene or ($C_2$–$C_6$) alkenylene; where said alkyl and aryl moieties of said R groups are unsubstituted or substituted with one or more substituents independently selected from the group consisting of halo, hydroxy, $(C_1–C_5)$ alkyl, $(C_1–C_5)$ alkoxy, and trifluoromethyl; and $R^1$ is selected from the group consisting of hydrogen; $(C_1–C_6)$ alkyl; phenyl; and $(C_3–C_7)$ cycloalkyl; wherein said alkyl and phenyl $R^1$ groups are unsubstituted or substituted with up to 3 substituents independently selected from the group consisting of methyl, ethyl, trifluoromethyl, and halo;

comprising:

(a) reacting a compound of Formula (Ia):

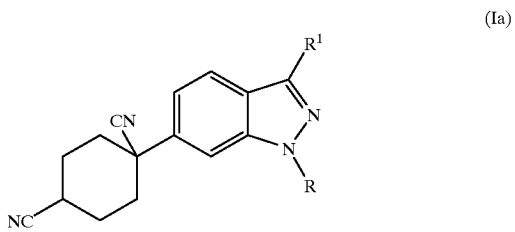

wherein R and $R^1$ are as defined above, with an alcohol of Formula (Ib-A) and an acid of Formula (Ib-B):

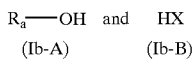

where $R_a$ is as defined above; and HX is an acid selected from the group consisting of hydrobromic acid; hydrochloric acid; sulfuric acid; sulfonic acid; and aliphatic and aromatic sulfonic acids selected from the group consisting of methanesulfonic acid, trifluoromethanesulfonic acid, benzenesulfonic acid, benzylsulfonic acid, p-toluene sulfonic acid, and camphorsulfonic acid, which results in the formation of an imidate of Formula (Ic):

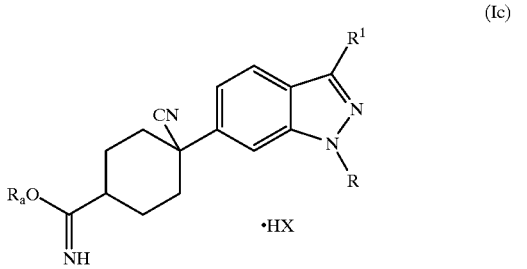

and (b) hydrolyzing said imidate of Formula (Ic) which results in the formation of said compound of Formula (I).

2. A method according to claim 1 wherein $R_a$ is selected from the group consisting of hydrogen; $(C_1–C_6)$ alkyl; phenyl and benzyl wherein said phenyl and benzyl groups are unsubstituted or substituted with one or two substituents selected from the group consisting of methyl, ethyl, iso-propyl, methoxy, Br and Cl; R is selected from the group consisting of cyclohexyl; cyclopentyl; cyclobutyl; methylene-cyclopropyl; iso-propyl; phenyl; and 4-fluorophenyl; and $R^1$ is selected from the group consisting of $(C_1–C_2)$ alkyl unsubstituted or substituted with up to three fluorines.

3. A method according to claim 2 wherein $R_a$ is selected from the group consisting of hydrogen; ethyl; propyl; iso-propyl; phenyl; benzyl; 3,5-dimethylphenyl; 3,5-dimethylbenzyl; 4-iso-propylphenyl; 4-iso-propylbenzyl; 4-bromophenyl; and 4-bromobenzyl; R is cyclohexyl; and $R^1$ is ethyl.

4. A method according to claim 1 wherein said compound of Formula (I) is cis-4-cyano-4-(1-cyclohexyl-3-ethyl-1H-indazol-6-yl)cyclohexanecarboxylic acid ethyl ester.

5. A method of preparing a compound of Formula (I):

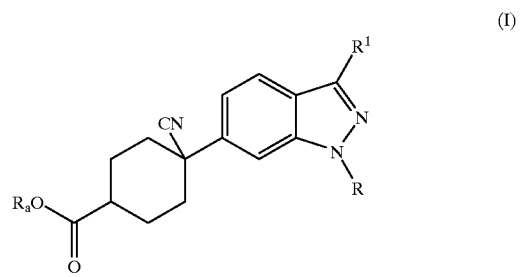

wherein $R_a$ is selected from the group consisting of hydrogen; $(C_1–C_6)$ alkyl; phenyl; and $(C_1–C_3)$ alkyl-phenyl wherein said phenyl groups are unsubstituted or substituted with one or two substituents selected from the group consisting of —$(C_1–C_4)$ alkyl; —$O(C_1–C_3)$ alkyl; Br; and Cl;

R is selected from the group consisting of hydrogen; $(C_1–C_6)$ alkyl; —$(CH_2)_n(C_3–C_7)$ cycloalkyl wherein n is 0 to 2; and —$(Z')_b(C_6–C_{10})$ aryl wherein b is independently 0 or 1 and Z' is $(C_1–C_6)$ alkylene or $(C_2–C_6)$ alkenylene; wherein said alkyl and aryl moieties of said R groups are unsubstituted or substituted with one or more substituents independently selected from the group consisting of halo; hydroxy; $(C_1–C_5)$ alkyl; $(C_1–C_5)$ alkoxy; and trifluoromethyl;

and $R^1$ is selected from the group consisting of hydrogen; $(C_1–C_6)$ alkyl; phenyl; and $(C_3–C_7)$ cycloalkyl; wherein said alkyl and phenyl $R^1$ groups are unsubstituted or substituted with up to 3 substituents independently selected from the group consisting of methyl; ethyl; trifluoromethyl; and halo;

comprising:

(a) reacting a compound of Formula (Id):

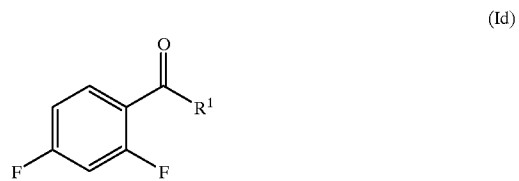

wherein R¹ is as defined above, with a hydrazine of Formula (Ie):

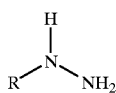
(Ie)

wherein R is as defined above, which results in the formation of a compound of Formula (If)

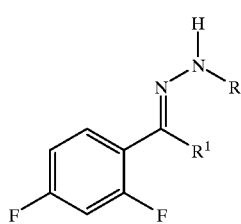
(If)

wherein R and R¹ are as defined above, followed by:
(b) heating said compound of Formula (If) to give by ring closure an indazole of Formula (Ig):

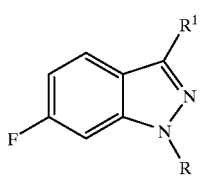
(Ig)

wherein R and R¹ are as defined above, followed by:
(c) reacting said indazole of Formula (Ig) with cyclohexane-1,4-dicarbonitrile of Formula (Ih):

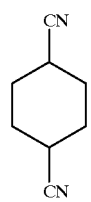
(Ih)

which results in the formation of a compound of Formula (Ia):

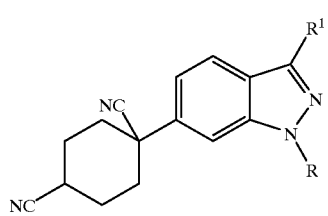
(Ia)

wherein R and R¹ are as defined above; followed by:
(d) reacting said compound of Formula (Ia) with an alcohol of Formula (Ib-A) and an acid of Formula (Ib-B):

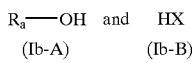

wherein $R_a$ is as defined above; and HX is an acid selected from the group consisting of hydrobromic acid; hydrochloric acid; sulfuric acid; sulfonic acid; and aliphatic and aromatic sulfonic acids selected from the group consisting of methanesulfonic acid, trifluoromethanesulfonic acid, benzenesulfonic acid, benzylsulfonic acid, p-toluene sulfonic acid, and camphorsulfonic acid, which results in the formation of an imidate of Formula (Ic):

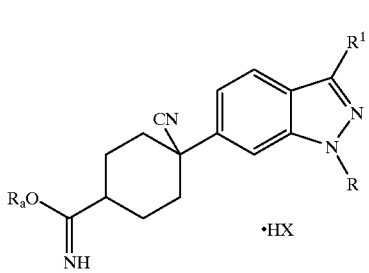
(Ic)

and
(e) hydrolyzing said imidate of Formula (Ic) which results in the formation of said compound of Formula (I).

6. A method according to claim 5 wherein $R_a$ is selected from the group consisting of hydrogen; ($C_1$–$C_6$) alkyl; phenyl; and benzyl wherein said phenyl and benzyl groups are unsubstituted or substituted with one or two substituents selected from the group consisting of methyl, ethyl, isopropyl, methoxy, Br and Cl; R is selected from the group consisting of cyclohexyl; cyclopentyl; cyclobutyl; methylene-cyclopropyl; iso-propyl; phenyl; and 4-fluorophenyl; and R¹ is selected from the group consisting of ($C_1$–$C_2$) alkyl unsubstituted or substituted with up to three fluorines.

7. A method according to claim 6 wherein $R_a$ is hydrogen; ethyl; propyl; iso-propyl; phenyl; benzyl; 3,5-dimethylphenyl; 3,5-dimethylbenzyl; 4-iso-propylphenyl; 4-iso-propylbenzyl; 4-bromophenyl; or 4-bromobenzyl; R is cyclohexyl; and R¹ is ethyl.

8. A method according to claim 5 wherein said compound of Formula (I) is cis-4-cyano-4-(1-cyclohexyl-3-ethyl-1H-indazol-6-yl)cyclohexanecarboxylic acid ethyl ester.

* * * * *